(12) United States Patent  
Trembly (10) Patent No.: US 9,131,984 B2  
(45) Date of Patent: Sep. 15, 2015

(54) THERMOKERATOPLASTY SYSTEMS (75) Inventor: B. Stuart Trembly, Hanover, NH (US)

(73) Assignee: The Trustees of Dartmouth College, Hanover, NH (US)

( * ) Notice: Subject to any disclaimer, the term of this patent is extended or adjusted under 35 U.S.C. 154(b) by 1382 days.

(21) Appl. No.: 12/714,032

(22) Filed: Feb. 26, 2010

(65) Prior Publication Data

US 2010/0160907 A1  Jun. 24, 2010

Related U.S. Application Data

(63) Continuation of application No. 11/688,146, filed on Mar. 19, 2007, now Pat. No. 7,713,268, which is a continuation of application No. 10/730,327, filed on Dec. 8, 2003, now Pat. No. 7,192,429, which is a continuation-in-part of application No. 10/314,670, filed on Dec. 9, 2002, now Pat. No. 7,377,917.

(51) Int. Cl.
| | |
|---|---|
| *A61B 18/04* | (2006.01) |
| *A61B 18/14* | (2006.01) |
| *A61B 18/18* | (2006.01) |
| *A61F 9/007* | (2006.01) |
| *A61B 17/00* | (2006.01) |
| *A61B 18/00* | (2006.01) |
| *A61F 9/013* | (2006.01) |

(52) U.S. Cl.
CPC ............ *A61B 18/1815* (2013.01); *A61B 18/18* (2013.01); *A61F 9/007* (2013.01); *A61F 9/0079* (2013.01); *A61B 2017/00084* (2013.01); *A61B 2018/00023* (2013.01); *A61F 9/013* (2013.01)

(58) Field of Classification Search
CPC ........ A61B 18/00; A61B 18/04; A61B 18/08; A61B 18/12; A61B 18/14; A61B 2018/146; A61B 2018/147
USPC ........ 606/4, 5, 27–35, 38, 41, 42, 50; 607/96, 607/98–104, 108
See application file for complete search history.

(56) References Cited

U.S. PATENT DOCUMENTS

| | | |
|---|---|---|
| 1,108,686 A | 8/1914 | Bonis |
| 1,364,148 A | 1/1921 | Springer |
| 2,126,070 A | 4/1938 | Wappler |
| 2,347,915 A | 5/1944 | Landauer |

(Continued)

FOREIGN PATENT DOCUMENTS

WO  0422112 B1  7/1996

OTHER PUBLICATIONS

Related U.S. Appl. No. 11/932,821, filed Oct. 31, 2007.

(Continued)

*Primary Examiner* — Ahmed Farah  
(74) *Attorney, Agent, or Firm* — Lathrop & Gage LLP (57) ABSTRACT

The present invention provides applicators for performing thermokeratoplasty. One embodiment of such applicators includes a pair of electrical conducting elements electrically separated by a selected distance and extending from a proximal end to a distal end. The electrical conducting elements define, at the distal end, a contact surface that is positionable at a cornea. At least one of the electrical conducting elements is divided into a plurality of discrete sections extending from the proximal end to the distal end. The discrete sections are selectively and separately actuated by a controller according to one or more variable characteristics to deliver energy to the cornea.

17 Claims, 7 Drawing Sheets

(56) References Cited

U.S. PATENT DOCUMENTS

| | | | | |
|---|---|---|---|---|
| 2,525,381 | A | 10/1950 | Tower | |
| 3,237,623 | A | 3/1966 | Gordon | |
| 3,307,533 | A | 3/1967 | Meredith et al. | |
| 3,948,269 | A | 4/1976 | Zimmer | |
| 3,978,864 | A | 9/1976 | Smith et al. | |
| 3,991,770 | A | 11/1976 | LeVeen | |
| 4,003,383 | A | 1/1977 | Bruck | |
| 4,014,333 | A | 3/1977 | McIntyre | |
| 4,030,480 | A | 6/1977 | Meyer | |
| 4,140,130 | A | 2/1979 | Storm, III | |
| 4,326,529 | A * | 4/1982 | Doss et al. | 606/41 |
| 4,381,007 | A * | 4/1983 | Doss | 606/27 |
| 4,528,991 | A | 7/1985 | Dittmar et al. | |
| 4,881,543 | A | 11/1989 | Trembly et al. | |
| 5,263,951 | A | 11/1993 | Spears et al. | |
| 5,368,590 | A | 11/1994 | Itoh | |
| 5,437,658 | A | 8/1995 | Muller et al. | |
| 5,458,596 | A | 10/1995 | Lax et al. | |
| 5,641,357 | A | 6/1997 | Yamada et al. | |
| 5,749,871 | A | 5/1998 | Hood et al. | |
| 5,779,696 | A | 7/1998 | Berry et al. | |
| 5,948,011 | A | 9/1999 | Knowlton | |
| 6,024,095 | A | 2/2000 | Stanley, III | |
| 6,053,909 | A * | 4/2000 | Shadduck | 606/3 |
| 6,104,942 | A | 8/2000 | Kruger | |
| 6,149,620 | A | 11/2000 | Baker et al. | |
| 6,149,643 | A | 11/2000 | Herekar et al. | |
| 6,159,205 | A | 12/2000 | Herekar et al. | |
| 6,224,593 | B1 | 5/2001 | Ryan et al. | |
| 6,364,875 | B1 | 4/2002 | Stanley, III | |
| 6,413,255 | B1 | 7/2002 | Stern | |
| 6,461,354 | B1 | 10/2002 | Olsen et al. | |
| 6,482,201 | B1 | 11/2002 | Olsen et al. | |
| 6,485,486 | B1 | 11/2002 | Trembly et al. | |
| 6,491,688 | B1 | 12/2002 | Lin et al. | |
| 6,520,956 | B1 | 2/2003 | Huang | |
| 6,567,688 | B1 | 5/2003 | Wang | |
| 6,623,454 | B1 | 9/2003 | Eggers et al. | |
| 6,673,069 | B1 | 1/2004 | Hood | |
| 6,694,173 | B1 | 2/2004 | Bende et al. | |
| 6,773,431 | B2 | 8/2004 | Eggers et al. | |
| 6,890,332 | B2 * | 5/2005 | Truckai et al. | 606/41 |
| 6,939,344 | B2 | 9/2005 | Kreindel | |
| 7,044,945 | B2 | 5/2006 | Sand | |
| 7,094,215 | B2 | 8/2006 | Davison et al. | |
| 7,192,429 | B2 | 3/2007 | Trembly | |
| 2002/0002369 | A1 | 1/2002 | Hood | |
| 2002/0042612 | A1 | 4/2002 | Hood et al. | |
| 2002/0099363 | A1 | 7/2002 | Woodward et al. | |
| 2002/0143322 | A1 | 10/2002 | Haghighi | |
| 2002/0173777 | A1 | 11/2002 | Sand | |
| 2003/0028228 | A1 | 2/2003 | Sand | |
| 2003/0163178 | A1 * | 8/2003 | Davison et al. | 607/101 |
| 2005/0107692 | A1 | 5/2005 | Li et al. | |
| 2005/0197657 | A1 | 9/2005 | Goth et al. | |
| 2005/0245949 | A1 | 11/2005 | Goth et al. | |
| 2007/0161976 | A1 | 7/2007 | Trembly | |
| 2010/0256626 | A1 * | 10/2010 | Muller et al. | 606/34 |

OTHER PUBLICATIONS

Trembly, B.S.; Hashizume, N.; and Moodie, K.S.; "Microwave Thermal Keratoplasty for Myopia: Keratoscopic Evaluation in Porcine Eyes" Journal of Refractive Surgery, pp. 682-688, 2001.

J.C. Lin, on Microwave-Induced Hearing Sensation. IEEE Transactions on Microwave Theory and Techniques. MTT-25 (1977) pp. 605-613.

G. Ku; L.V. Wang, Combining Microwave and Ultrasound: Scanning Thermoacoustic Tomography. Proceedings of the 22nd Annual EMBS International Conference, Jul. 2000, Chicago, IL.

Selected File History from related U.S. Appl. No. 11/688,146.

Selected File History from related U.S. Appl. No. 10/730,327.

Selected File History from related U.S. Appl. No. 10/314,670.

International Search Report issued Jun. 11, 2004 in related PCT Application Serial No. PCT/US03/38978.

International Preliminary Examination Report issued Mar. 22, 2005 in related PCT Application Serial No. PCT/US03/38978.

EP Rule 109 and 110 Communication issued Aug. 5, 2005 in related European Application No. 03796799.9.

Response to EP Rule 109 and 110 Communication issued Aug. 5, 2005 in related European Application No. 03796799.9 filed Sep. 9, 2005.

* cited by examiner

THERMOKERATOPLASTY SYSTEMS

REFERENCE TO RELATED APPLICATIONS

This application is a continuation of U.S. patent application Ser. No. 11/688,146, filed Mar. 19, 2007, now U.S. Pat. No. 7713268 which is a continuation of U.S. patent application Ser. No. 10/730,327, filed Dec. 8, 2003, now U.S. Pat. No. 7,192,429, which was a continuation-in-part of U.S. patent application Ser. No. 10/314,670, filed Dec. 9, 2002, now U.S. Pat. No. 7,377,917, each of which is incorporated by reference herein.

BACKGROUND

The invention pertains to the field of keratoplasty and, more particularly, to thermokeratoplasty, especially electrically-induced thermokeratoplasty such as radio frequency or microwave thermokeratoplasty.

The object of keratoplasty is to correct vision by reshaping of the cornea. For nearsighted persons, this reshaping involves flattening that ideally decreases the refractive power of the eye and causes the image to focus upon the retina, as opposed to focusing images in front of the retina. Invasive surgical procedures, such as laser-assisted in-situ keratonomileusis (LASIK) may be used, but there are associated complications, such as the dry eye syndrome associated with severing of corneal nerves, and the need for a healing period after surgery.

Thermokeratoplasty is a noninvasive procedure that may be used to correct the vision of nearsighted persons by flattening the cornea. Generally, the cornea is heated to a point where collagen fibers in the cornea shrink, which results in stresses that tend to reshape the cornea. Thermokeratoplasty may be performed by the use or absorption of electrical energy, which is typically cycled in the microwave or radio frequency band for this purpose. Microwave thermokeratoplasty uses a near-field microwave applicator to apply energy to the cornea, raising the corneal temperature. At about 60° C., the collagen fibers in the cornea shrink, and the onset of shrinkage is sudden. Resultant stresses from this shrinkage reshape the corneal surface. Application of energy in this manner may cause reshaping that flattens the central cornea when the energy is applied in circular or ring-shaped patterns around the pupil.

Devices and methodologies for microwave thermokeratoplasty are shown and described in U.S. Pat. No. 4,881,543 to Trembly et al., which is hereby incorporated by reference to the same extent as though fully replicated herein. The microwave applicator comprises an open-ended coaxial antenna driven at 915 MHz or 2540 MHz with an internal coolant system that drives flow of saline coolant transverse to the antenna axis. The '543 patent advances the art by providing applied electrical field theory for open-ended coaxial applicators and the related specific absorption rate, e.g., by using the Swicord and Davis technique in addition to heat transfer theory involving the Nusselt number, the Reynolds Number, and the dimensions of the gap between the antenna and the cornea.

Generally, these devices and methodologies are referred to as "microwave thermokeratoplasty" even though emissions at 915 MHz are slightly below the 1 GHz cutoff that many persons use to identify the microwave band. The term "radio frequency thermokeratonomy" may be used to describe energetic keratoplasty by excitation at lower frequencies. Microwave and radio frequency thermokeratoplasty may be used to achieve similar results, but the applied energy affects the tissue in different ways according to the various theories of operation where the radio frequency heating of tissue has a larger resistive heating component.

Figure 1:
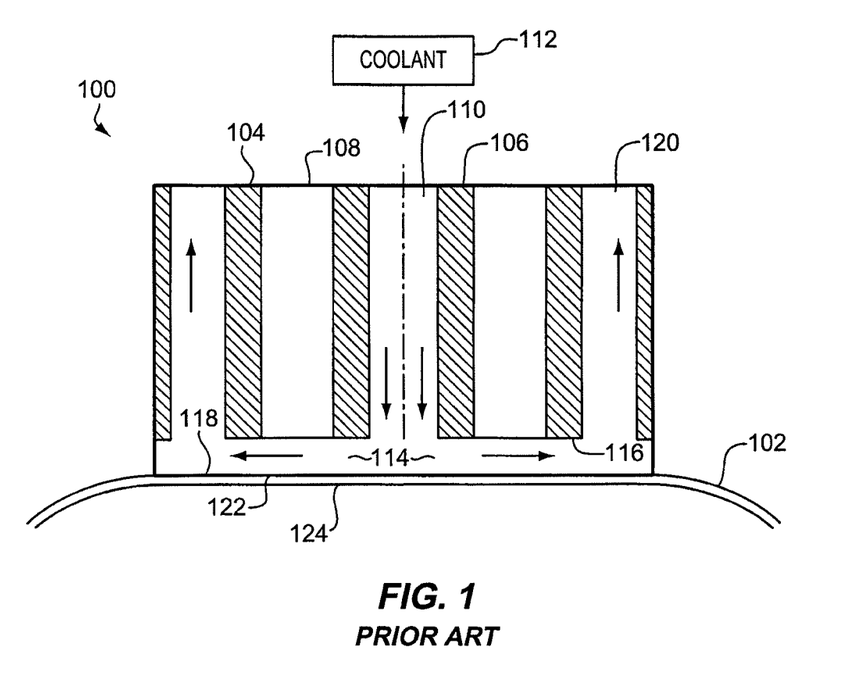
FIG. 1 shows a prior art microwave applicator.

FIG. 1 is a side midsectional view illustrating a conventional microwave applicator 100 deployed for use in microwave thermokeratoplasty operations on a cornea 102. An oscillator drives microwave field emissions on concentric microwave conductors, such as conductive metal tubes 104 and 106. A dielectric 108 fills space between the tubes 104 and 106. A central passageway 110 permits the flow of coolant 112 into a flow gap 114 of about 0.3 mm to 0.5 mm between a terminal antenna end 116 and a Mylar™ (a trademark of E. I. du Pont de Nemours and Company Corporation, of Wilmington, Del.) film 118. The flow gap 114 places the central passageway 110 in fluidic communication with exit annulus 120 for circulation of coolant 112. The Mylar™ film 118 comes into direct contact with cornea 102 at interface 122, which may optionally have a concave down configuration adapted so as not to over-stress the cornea 102 by excessive flattening.

As shown in FIG. 1, the configuration of applicator 100 provides a microwave field that distributes itself downward through the coolant in flow gap 114 and into the cornea 102. The tubes 104 and 106 form an inefficient near-field applicator ideally having a penetration depth of less than about one millimeter, as opposed to a true antenna that can launch a wave. The small value of microwave penetration depth is an intentional design feature that is intended to protect the endothelium or back surface 124 of cornea 102 because the endothelium 124 is regarded to be incapable of regeneration after thermal damage. Coolant 112 flowing in the flow gap 114 cools the cornea at interface 122 by forced convection. The Mylar™ film 118 retains the coolant 112 in flow gap 114 and also prevents the flow of electrical current from tubes 104 and 106 into the cornea 102. By balancing the heating effects of applied microwave field against the cooling benefits of coolant 112, a local maximum of temperature is produced at near mid-depth of the cornea 102 while protecting the corneal epithelium (front surface) and the endothelium 124 (rear surface) from thermal damage.

A number of problems have arisen in use of prior microwave applicator devices. Chiefly, the amount of applied energy is unpredictably related in terms of a precise biological effect, such as by administering energy to produce a predetermined amount of vision correction. The thermal flux at depth in the cornea can be calculated according to theory with a high degree of precision; however, the thermal flux is not calibrated to a measurable biological effect in terms of an applied treatment modality. For example, it is undetermined what level of thermal flux is required to flatten a particular cornea to a desired level of diopter adjustment. This uncertainty is exacerbated by the characteristically sudden onset of thermally-induced shrinkage in the cornea. There is no clear way to determine in the course of treatment if, for example, the outermost layer of corneal cells known as the epithelium is undergoing thermal damage as a result of treatment, and this uncertainty can lead to a painful period of healing while the epithelium regenerates. Critical, small dimensions in the applicators may vary with machining errors, assembly or use, most notably in the dimensions of flow gap 114 for the coolant. Even small machining errors in these dimensions result in the applicator producing asymmetric treatment rings and associated astigmatic effects on the "corrected" vision resulting from use of these devices.

There is a need to improve the predictability of effectiveness of microwave thermokeratoplasty applicators and to reduce the unintended harm that such devices may produce.

SUMMARY OF THE INVENTION

The present invention overcomes the problems outlined above and advances the art by providing a microwave application device and system that is less likely to produce unintended harm, such as astigmatic effects and burning of epithelial or endothelial corneal tissues. The device and system are advantageously configurable for use in treatment modalities that are predictable or verifiable in their effects upon vision correction.

The thermokeratoplasty system may include an energy transmitter used for cornea-based vision correction modalities. According to the various instrumentalities and embodiments of this system, an improvement to prior systems may comprise a sensor that is configured to measure a physical variable in an eye as the eye is affected by a thermokeratoplasty operation and to provide a sensor signal representative of the physical variable. A feedback circuit may be adapted to receive the sensor signal and analyze the sensor signal to determine when a treatment modality has achieved an intended effect.

By way of example, the sensor may be configured to measure the physical variable as corneal temperature, either as a surface temperature or temperature at depth in the cornea. The sensor may also or alternatively be configured to measure the physical variable as heat flux in the cornea, mechanical stress of the cornea, mechanical strain of the cornea or an electrical property of the cornea, such as the phenomenon of conductivity or permittivity. The sensor may be configured to measure the physical variable as a mechanical property of the cornea, for example, mass density, modulus of elasticity, or a change in optical opacity associated with shrinkage of collagen in the cornea.

The sensor signal may derive from many forms of measurement. For example the sensor signal may embody information concerning a quantity of electrical current passing through the cornea, an electrical voltage applied to the cornea, and/or electromagnetic energy applied to the cornea, such as reflected energy, transmitted energy, and energy received from tissue. The electromagnetic energy may be measured as an optical birefringence phenomenon and/or a microwave radiometry phenomenon. Ultrasonic energy may also be applied to the cornea for use in measurements, for example, as measurements of reflected energy, transmitted energy, and/or energy received from tissue.

The sensor signal may embody information obtained from a mechanical transducer, such as a piezo-resistive or piezoelectric device that is oriented to quantify parameters including corneal elongation, corneal compression, corneal displacement, corneal velocity, corneal acceleration, local slope, local curvature, global slope, global curvature, corneal stress, and corneal pressure. These measurements may pertain to scalar, vector, or tensor variables measured at the surface of the cornea or at depth in the cornea. Alternatively, a thermal transducer may be used to determine, for example, temperature and heat flux at the surface of the cornea or at depth in the cornea. Useful types of thermal transducers may include, without limitation, a thermocouple, a thermistor, and a sub-millimeter-scale device.

The feedback circuitry may operate by using signals and signal processing circuits, such as by processing a sensor signal according to an empirical correlation that relates the sensor signal to a predetermined vision correction effect. The feedback circuitry may also operate by processing the sensor signal to determine when the physical variable has been adjusted to achieve a predetermined quantity of the physical variable, such as a predetermined level of birefringence.

According to various instrumentalities and embodiments herein, at least one additional sensor may be used to provide an additional sensor signal. The feedback circuitry may be configured to process the sensor signals in combination to determine when the treatment modality has achieved the intended effect as a function of the respective signals.

In one embodiment, the microwave or radio frequency applicator is configured for direct contact with the cornea without a coolant flow gap between the microwave or radio frequency applicator and the cornea. The microwave applicator may include a plurality of discrete sectors that are optionally actuated by control circuitry in a selective and independent manner for the emission of microwave or radio frequency energy according to the treatment modality. Program instructions for the control circuitry may, for example, provide a capability to change the actuation of one or more of the plurality of discrete sectors on the basis of the sensor signal. To compliment this functionality, the sensor may include an array of sensors each allocated to a corresponding one of the plurality of discrete sectors and linked to the feedback circuitry.

Other instrumentalities involve special features of a radio frequency or microwave thermokeratoplasty applicator. A plurality of concentric tubes each may have a top end and a bottom surface configured to apply electrical energy for keratoplasty operations. A dielectric material may separate the plurality of concentric tubes from one another. A cooling system may be configured to cool the applicator during keratoplasty operations without flowing coolant beneath the bottom surface 116. This type of cooling system eliminates systematic errors that are introduced by virtue of having a flow gap of varying dimensions, e.g., flow gap 114 (shown in FIG. 1). For example, the cooling system may comprise a Peltier effect or thermoelectric cooling device or a system for circulating liquid coolant in upper regions of the applicator, but not bottom regions proximate the bottom surface of the applicator. A vacuum positioning system may optionally be used to retain the applicator on a cornea.

In use, the thermokeratoplasty system facilitates a thermokeratoplasty modality that employs an energy transmitter used for cornea-based vision correction modalities. The method of operation may, for example, include applying microwave or radio-frequency energy or other heat transmitting energy, sensing a physical variable in an eye as the eye is affected by a thermokeratoplasty operation to provide a sensor signal representative of the physical variable, receiving the sensor signal, and analyzing the sensor signal to determine when a treatment modality has achieved an intended effect.

In another aspect, the present invention provides an applicator for performing thermokeratoplasty that includes a pair of microwave conducting elements that extend from a proximal end to a distal end, and that are separated from one another by a selected distance. A dielectric insulator is disposed between the conducting elements to provide electrical insulation therebetween. The application of a microwave signal across the conducting elements at the proximal end causes generation of a microwave field at the distal end. The conducting elements are configured to have direct contact with corneal tissue upon placement of the applicator's distal end on a subject's cornea.

In a related aspect, the surfaces of the conducting elements of the above applicator, which are configured to have direct contact with the cornea, are at least partially coated with a thermally conductive and electrically insulating material.

In further aspects, the present invention provides an applicator for performing thermokeratoplasty that includes a pair of elongated conductors, separated by a selected distance, that extend from a proximal end to a distal end. An insulator is disposed between the two conductors to provide electrical insulation of the conductors from one another. The applicator further includes a vacuum source having at least one vacuum passage that extends from the proximal end to the distal end. The vacuum source can apply suction to at least a portion of corneal tissue upon positioning of the applicator on a subject's cornea to facilitate the retention of the corneal tissue by the applicator.

In another aspect, the invention provides a system for performing thermokeratoplasty that includes an applicator having a proximal end and a distal end, a microwave generator for applying a microwave signal to the applicator's proximal end so as to generate a microwave radiation field at the applicator's distal end, and a controller coupled to the microwave generator for applying control signals thereto. The applicator includes at least a pair of microwave conducting elements that extend from the applicator's proximal end to its distal end, and are separated from one another by an electrical insulator. The conducting elements are configured to have direct contact with a subject's cornea when in use.

DETAILED DESCRIPTION

Figure 2:
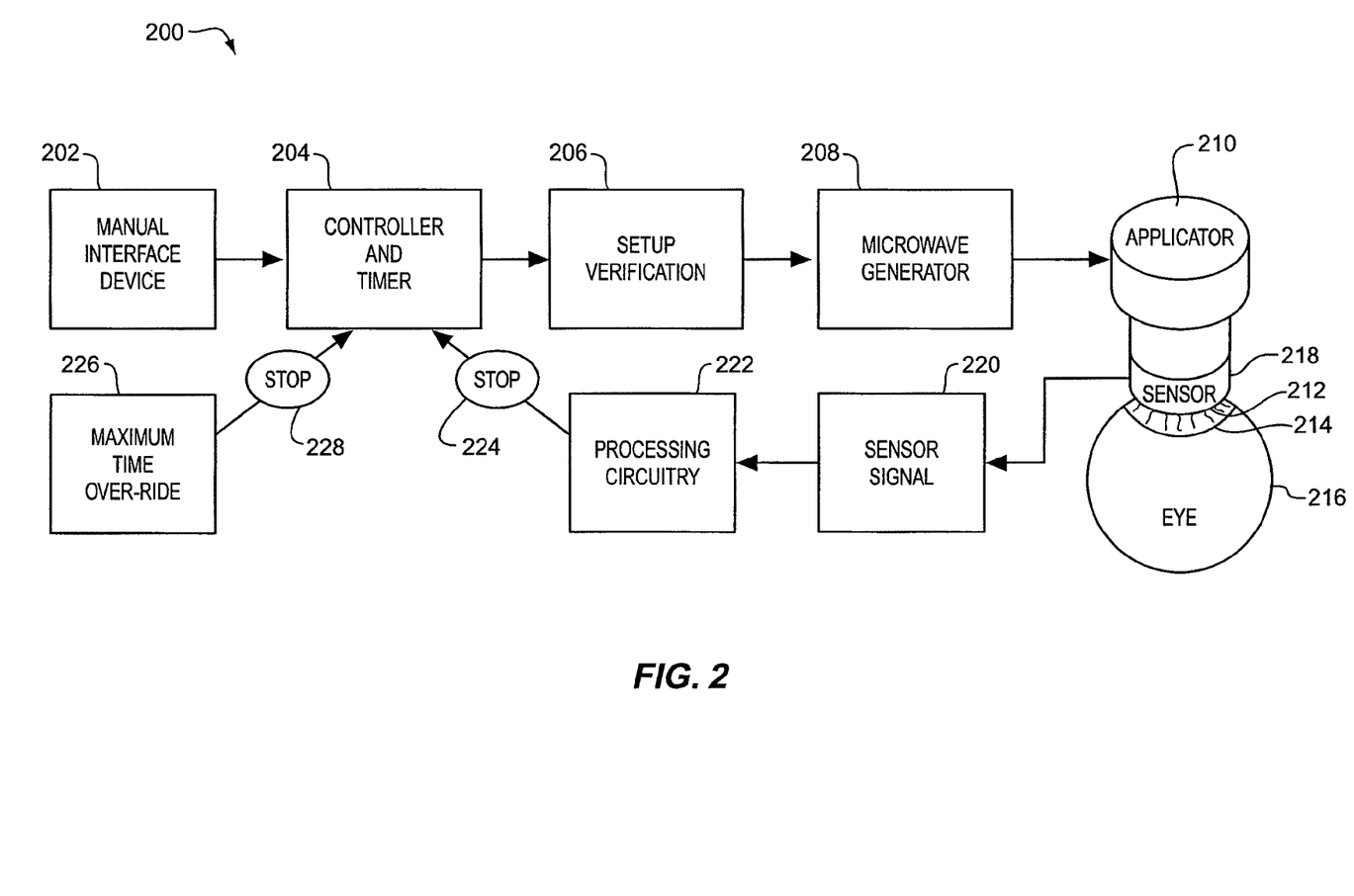
FIG. 2 is a block schematic diagram illustrating system components of a radio-frequency or microwave thermokeratoplasty system in accordance with the principles described herein.

In FIG. 2, there will now be shown and described, by way of example and not by limitation, a thermokeratoplasty system 200 that operates by sensing a physical variable in an eye and providing sensed feedback affecting a vision correction modality. A physician or other medical worker manually accesses an interface device 202, such as a computer keyboard, that facilitates the selection and/or initiation of a treatment modality. The interface device 202 may request manual input, such as a predetermined amount of diopter correction that is required for a particular patient, baseline measurements of physical variables, astigmatism measurements, wavelength of microwave radiation, intensity of microwave radiation, selection of a treatment modality by specific selection or class of modality, and/or goals for adjusted physical variables obtainable as a result of treatment.

A programmable controller 204 accepts program instructions that optionally access user input data or program selections from the interface device 202 and causes system 200 to implement a selected vision correction modality. Setup verification in step 206 may be a user-interactive process that verifies the modality and assures that system 200 is correctly positioned or configured for thermokeratoplasty operations. Once setup is verified, a generator, such as microwave or other electrical signal generator 208, produces energy that is useful for thermokeratoplasty purposes and supplies this energy, e.g., in the form of microwave or other oscillating energy, to an applicator 210. In some instances, a near-microwave emission of 915 MHz (approved by the FCC for medical use) is preferred to reduce system cost; however, the generator 208 may be operated at other frequencies, such as 2450 MHz, that are conventionally used and understood to have therapeutic benefits according to a desired modality. In turn, applicator 210 produces corresponding near-field effects 212 in cornea 214 of eye 216. Generally speaking, electrical energy useful in the present invention includes radiant electric energy at frequencies from about 100 kHz to 10 GigaHertz. In many applications, the preferred frequencies lie in the "microwave" region of the spectrum. As used herein, the term "microwave" is intended to encompass radiant electrical energy oscillating at frequencies ranging from about 100 MHz to about 10 GigaHz, more preferably from about 500 MHz to about 3000 MHz.

The cornea 214 and eye 216 inherently have one or more variable physical properties (i.e., physical variables) that may be affected by the microwave or radio-frequency near-field effects 212 and the consequent temperature elevation. These physical variables may be measured by a sensor 218 to provide a sensor signal 220 that embodies a direct or indirect measurement of the physical variables. Processing circuitry 222 may receive the signal 220 and analyze the same to determine if and when the modality has achieved a desired effect that is relevant to the intended or planned outcome of the modality. Processing circuitry 222 may generate a stop signal 224 that terminates treatment when the physical variable has been modified to within a predetermined range or value. Sensor 218 for use with the applicator 210 may be one or more of the sensors described above, such as:

a thin film or microelectronic thermal transducer; or a mechanical transducer, such as a piezoresistive or piezoelectric device, or a force-sensitive quartz resonator that quantifies corneal elongation or internal pressure.

In one embodiment, a safety mechanism is built into program instructions for controller 204 as a clock-based maximum time override 226 that generates a stop signal 228 at the termination of a safe time interval for the selected modality. This feature may assure that operation of the microwave generator 206 does not exceed a specified amount of time at any given level of output and is intended to avoid thermal damage to the corneal epithelium, and especially the endothelium.

Figure 3:
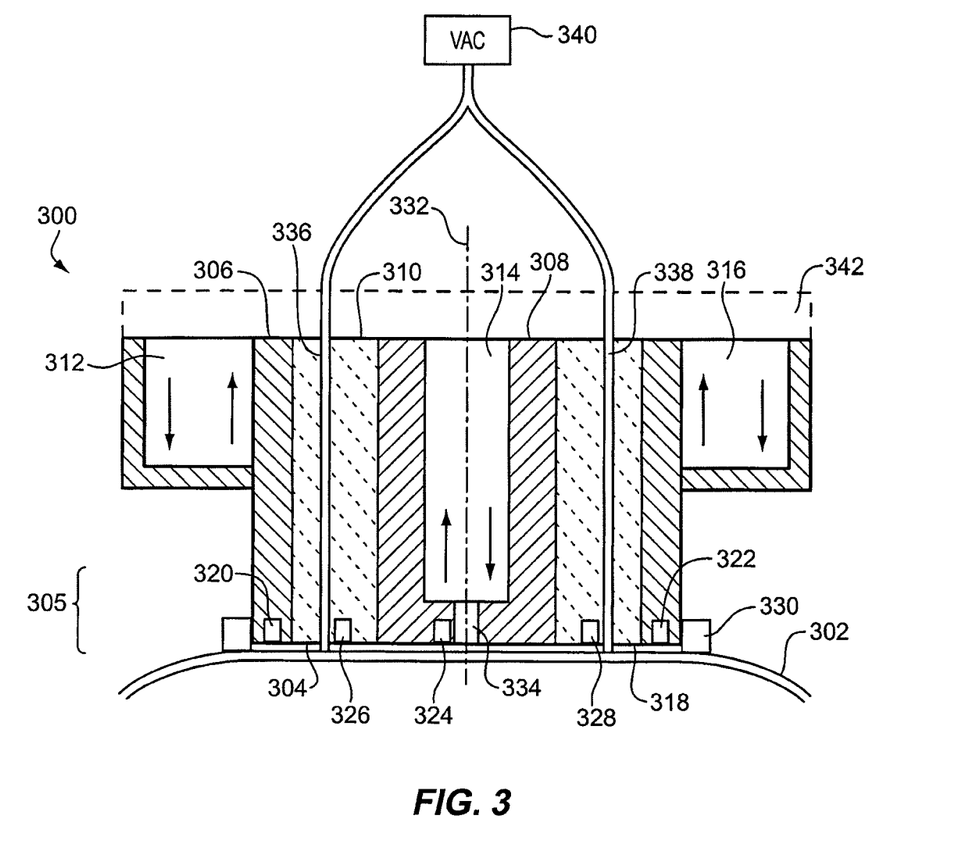
FIG. 3 is a side perspective midsectional view of one microwave applicator that is improved with respect to the prior art.

Most types of microwave thermokeratoplasty applicators 210 may be used generally in the aforementioned system 200, provided the applicator is fitted with the sensor 218. FIG. 3 depicts a side elevation midsectional view of a cylindrical applicator 300 that contains several improvements over the applicator 100 of FIG. 1. One such improvement is, for example, the absence of a flow gap between cornea 302 and a bottom surface 304 of applicator 300, such that no coolant circulates below applicator 300 or in the lower region 305, e.g., the bottom ten percent or so of applicator 300 proximate to cornea 302.

In one embodiment, an outer insulated microwave-conductive tube 306 circumscribes an inner insulated tube 308 that is also microwave conductive. Tubes 306 and 308 are concentric. A dielectric material 310 may separate tube 306 from tube 308. It should be appreciated that the term "tube" as used herein encompasses both cylindrical elements and metallic coatings that function like a free-standing conductive cylinder. For example, a microwave conductive tube can be a metallic coating on a nonmetallic, tubular-shaped, material. The spacing between tubes 306 and 308 controls penetration depth of microwave energy according to established microwave field theory. In one embodiment, chambers 312, 314, and 316, are configured for bidirectional coolant flow providing a predetermined amount of cooling from coolant (e.g., coolant 112, FIG. 1). Such flow is optionally regulated by controller 204 (see FIG. 2) to achieve a maximum temperature at mid-depth in cornea 302, for example, according to established thermal flux theory.

The outer diameter of the inner conductive tube 308 is preferably larger than the pupil of the patient's eye. The outer diameter of the inner conductor also may be selected so as to have a greater or lesser effect on the change in keratometry induced by the microwave keratoplasty treatment. The inner diameter of the outer conductive tube 306 is selected so as to generate a desired gap between the two conductive tubes. In some embodiments, this gap is sufficiently small, e.g., in a range of about 0.1 mm to about 2.0 mm, so as to spare the endothelial layer of the cornea (posterior surface) from exposure to elevated temperatures during corneal treatment by the applicator. By way of example, in some preferred embodiments of the applicator, the outer diameter of the inner conductor 308 ranges from about 2 to about 10 mm while the inner diameter of the outer conductor 306 ranges from about 2.1 to about 12 mm.

The inner and the outer conductive tubes 306 and 308 can be formed, for example, of aluminum, stainless steel, brass, copper, other metals, metal-coated plastic, or any other suitable material. In some embodiments, at least a portion of each of the conductive tubes 306 and 308 is covered with an electrical insulator to prevent, for example, concentration of electrical current in the area of contact between the corneal tissue and the conductors. In some embodiments, the conductive tubes, or at least a portion thereof, are coated with a nonmetallic material that can function both as an electrical insulator as well as a thermal conductor. The coating can be accomplished by employing, for example, a vapor deposition or a spray process. Alternatively, a nonmetallic electrically insulating layer can be bonded to the metallic conductive tubes by employing, e.g., a hot isostatic press method, powder metallurgy with differential layers, or frictional welding. In other embodiments, metallic conductive tubes 306 and 308, or a portion thereof, can be covered with plastic deposited thereon by employing, for example, a dipping process, a spinning process, or any other suitable process known in the art.

Further, as described in more detail below, a coating disposed on the conductive tubes 306 and 308 can exhibit a graded thermal conductivity. For example, a metal matrix composite material, such as alumina having a differential concentration of aluminum oxide particles in an aluminum matrix, can be utilized as the coating material. In some embodiments, the coating material closest to the cornea and the outside surface of the applicator has the highest thermal conductivity, e.g., the highest concentration of aluminum oxide particles when the coating material is alumina, while the other portions of the coating, e.g., the portions that coat central section of the applicator, contain a lower thermal conductivity, e.g., a lower concentration of aluminum oxide particles.

With continued reference to FIG. 3, a bottom dielectric layer 318 may protect cornea 302 from deleterious temperature effects of electrical conduction current that, otherwise, would flow into cornea 302 from the tubes 306 and 308. The bottom dielectric layer 318 may separate bottom surface 304 from cornea 302. The dielectric layer 318 may be thin enough to minimize interference with microwave emissions and thick enough to prevent superficial deposition of electrical energy by flow of conduction current; superficial flow of a conduction current could interfere with the goal of achieving a mid-depth maximum temperature in cornea 302. By way of example, the dielectric layer 318 may be a biocompatible material, such as Teflon, deposited to a thickness of about 0.002 inches. Alternatively, the dielectric layer 318 may be a thermal conductor, such as hard-coat anodizing.

Upon positioning of the applicator on a patient's cornea, the microwave conducting tubes 306 and 308 have "direct contact" with the corneal tissue. The phrase "direct contact", as used herein, indicates that no fluid, such as, a coolant fluid, flows between the bottom surfaces of the microwave conductive tubes 306 and 308 and the corneal tissue. The conducting tubes can have a direct contact with the corneal tissue even if a thin layer of a material, such as, the dielectric layer 318, separates the bottom surfaces of the conducting tubes from the corneal tissue so long as the interposing layer does not substantially interfere with the strength of the microwave field established between the conducting tubes, and hence its penetration into the corneal tissue. In other words, the interposing layer can be employed while maintaining direct contact between the conducting tubes and the corneal tissue so long as the interposing layer does not prevent generation of a desired heating pattern in the corneal tissue by exposure of the tissue to a microwave radiation field generated between the conducting tubes at the applicator's distal end.

Establishing a direct contact between the conducting tubes and the corneal tissue provides a number of advantages. For example, with direct contact, the pattern of microwave heating in tissue has substantially the same shape and dimension as the gap between the two microwave conductors. By contrast, when direct contact is prevented by the presence of a layer of fluid coolant of finite thickness flowing between the microwave conductors and tissue, the pattern of microwave heating in tissue may be, for example, a circle with a diameter less than that of the inner conducting tube or rod, rather than being an annulus with dimensions equal to that of the gap between the conductors. An annulus is a preferred heating pattern because the inner diameter of the heated annulus can be selected to be sufficiently large so as to avoid heating the central cornea overlying the pupil. Central heating of the cornea can be deleterious due to a temporary opacity that can be associated with such heating.

In addition, providing direct contact between the conductors and cornea eliminates potential deleterious effects associated with variability in the finite thickness of a layer of flowing coolant. For example, a layer of fluid coolant can have a thickness that varies by about 0.005 inches across the distal end of the application as a result of typical machining errors. Such a variation may comprise a significant fraction of a nominal thickness of the coolant layer because the nominal thickness may be selected to be sufficiently small so as to render the heating pattern geometrically similar to the gap between the conductors. For example, the nominal thickness of the layer of fluid coolant may be selected to be about 0.020 inches. In such a case, the actual thickness can vary between 0.015 inches to 0.02 inches (i.e., by about 33 percent) due to typical machining errors, thus causing the microwave heating to vary significantly across the applicator's distal end. In contrast, an applicator configuration providing direct contact eliminates such variations of microwave heating across the applicator's distal end, which is otherwise a sensitive function of the thickness of the coolant layer.

In some embodiments, the layer 318 is formed of a thermally conductive but electrically insulating material. In such embodiments, the thermal conductivity of the layer 318 can be in a range of about 0.1 W/(m °C.) to about 500 W/(m °C.), and more preferably, in a range of about 2 W/(m °C.) to about 200 W/(m °C.). By way of example, the layer 318 can be formed of anodized aluminum, having a thickness in a range of about 0.001 inches (about 0.025 mm) to about 0.002 inches (about 0.05 mm), that not only provides electrical insulation between the electrodes and the corneal tissue but also provides good thermal contact with the corneal tissue for extracting heat therefrom.

The sensor 218 (shown in FIG. 2) may be a type of sensor described above, and may, for example, comprise embedded microelectronic devices 320, 322 and/or 324 in the tubes 306 and 308, devices such as sensors 326 and/or 328 embedded in the dielectric material 310, or optional separate sensors such as sensor 330 deployed outside of applicator 300. Alternatively, the dielectric layer 318 is, for example, a grid of thin film transducers each operating as a wheatstone bridge. Where the applicator 300 is deployed with axis of symmetry 332 over a pupil, a transparent window 334 may be used to quantify the refractive effect of treatment with optical instrumentation, such as a videokeratoscope.

In one embodiment, vacuum passages 336 and 338 pass through the dielectric material 310, and connect to a vacuum source 340 for purposes of enhancing retention of applicator 300 in a fixed position relative to cornea 302 during treatment. The vacuum source 340 can apply a controlled amount of suction to the cornea to ensure firm and even contact of the applicator's bottom surface with the cornea.

In alternative embodiments, a liquid coolant is not required. Chambers 312, 314, and 316 may be filled with a heat sink in thermal communication with an optional thermoelectric cooler device 342 that operates, for example, using a Peltier effect under the control of controller 204.

Figure 4:
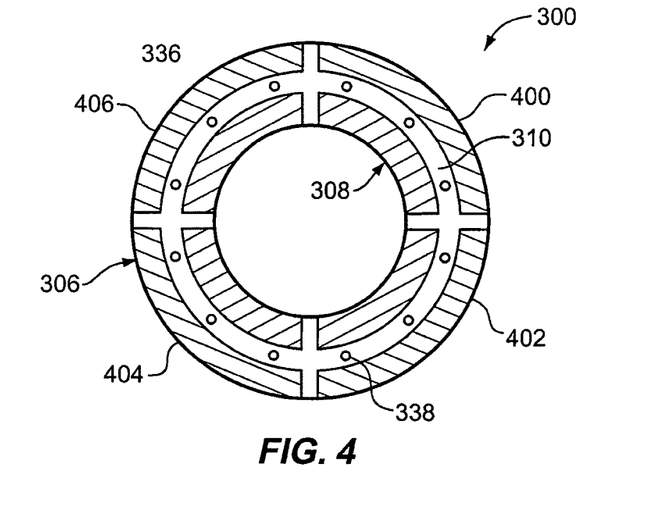
FIG. 4 is a top perspective midsectional view of the microwave applicator shown in FIG. 3.

FIG. 4 is a top midsectional view of applicator 300. Each of the tubes 306 and 308 may be divided into a plurality of discrete sectors or sections, which in FIG. 4 are quartile sections of coaxial extension, such as quartile sections 400, 402, 404, and 406 in the case of tube 306. Each of these sections 400-406 may be separately coupled with controller 204 (shown in FIG. 2) for individual operation where, for example, microwave radiation of different intensity, duty cycle, waveform, frequency, or duration may be applied to any one section, or the sections 400-406 may be driven wholly or partially in unison. There may be any number of sections separated by dielectric material 310 and any number of concentric tubes, such as tubes 306 and 308. The capability to drive discrete sections facilitates treatment of native astigmatism in the patient, and it offers further capacity not heretofore found, which is to provide modalites that are custom tailored to address a variety of diopter adjustments in optimized fashion by selectively providing more or less treatment energy to sections in a radially outboard pattern.

Figure 5:
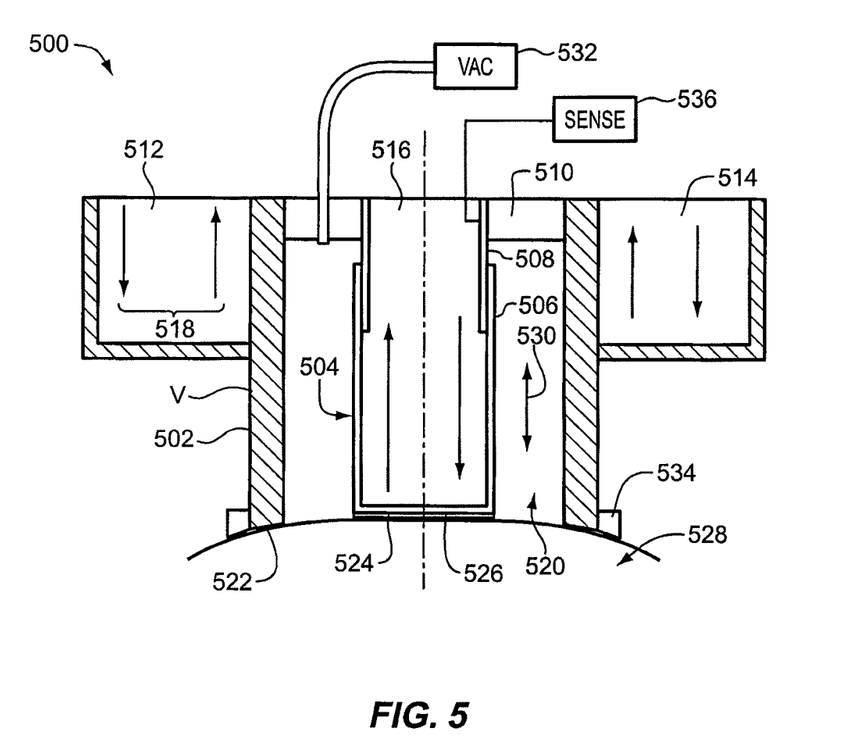
FIG. 5 is a side perspective midsectional view of one microwave thermokeratoplasty applicator that may be used in place of the applicator shown in FIG. 3.

FIG. 5 is a side elevation midsectional view of a cylindrical microwave or radio-frequency thermokeratoplasty applicator 500 that may be used in place of applicator 300. An outer insulated electrically-conductive tube 502 may circumscribe an inner telescoping insulated tube 504 that is also electrically-conductive. Inner tube 504 may be formed in at least two telescoping sections 506 and 508 that are in electrical contact with one another. The tubes 502 and 504 may be concentric. A dielectric material 510 may separate tube 502 from section 508. The spacing between tubes 502 and 504 controls penetration depth of microwave or radio-frequency energy according to established microwave and radio-frequency field theory. Generally, the near-field effects produce localized heating effects on corneal tissue without producing a radiation wave that is capable of heating the corneal endothelium to a point of damage. Chambers 512, 514, and 516 are configured for bidirectional coolant flow (e.g., as flow 518) generally as described with respect to applicator 300. An annular air gap 520 may surround the telescoping tube 504. Bottom surfaces 522 and 524 may be contoured to conform with an eye, e.g., generally to conform with a spherical shape established by ball-milling processes. Alternatively, such contoured surfaces can be curved, beveled or chamfered. For one embodiment, bottom surfaces 522 and 524 are coated with a material 526 that is both dielectric and heat conductive, such as Teflon powder coating material, or anodizing material. For example, in some embodiments, the tubes 502 and 504 are formed of aluminum and the anodizing material coating the bottom surfaces 522 and 524 includes a layer of aluminum oxide having a thickness, e.g., in a range of about 0.0005 inches to about 0.010 inches, and more preferably in a range of about 0.001 inches to about 0.002 inches. The material 526 may protect cornea 528 from deleterious temperature effects of electrical conduction current that, otherwise, would flow into cornea 528 from the tubes 502 and 504, according to principles described generally above with respect to applicator 300.

Section 504 may telescope axially over section 506, as shown by a double-headed arrow 530, to assure that material 526 is positioned in full contact with cornea 528. This sliding action may be facilitated by gravity or positive pressure exerted by coolant flowing in chamber 516. A vacuum pump 532 may also be used to exert a mild vacuum within chamber 516 to force this contact. Alternatively, a screw mechanism (not shown) may be positioned in air gap 520 to provide fixed and repeatable adjustments to the height of section 504.

Applicator 500 can include a sensor, e.g., sensor 218, which can, for example, include outside sensors 534 deployed outside of applicator 500 and/or embedded sensor devices not shown in FIG. 5. A second sensing device 536 may be used to sense whether full contact exists between the tubes 502, 504, and the cornea 528. Corneal tissue contains relatively high amounts of water and is conductive. Thus, a voltage V applied to outer tube 502 may be sensed by the second sensing device 536 as a resistance or capacitance. The magnitude of resistance or capacitance may be correlated to the amount of contact between applicator 500 and cornea 528. A signal from the second sensor 536 may be used as part of the feedback system through processor circuitry 222 (FIG. 2) or may be operated independently of the feedback system and used solely as a means to assure contact between applicator 500 and cornea 528.

Figure 6:
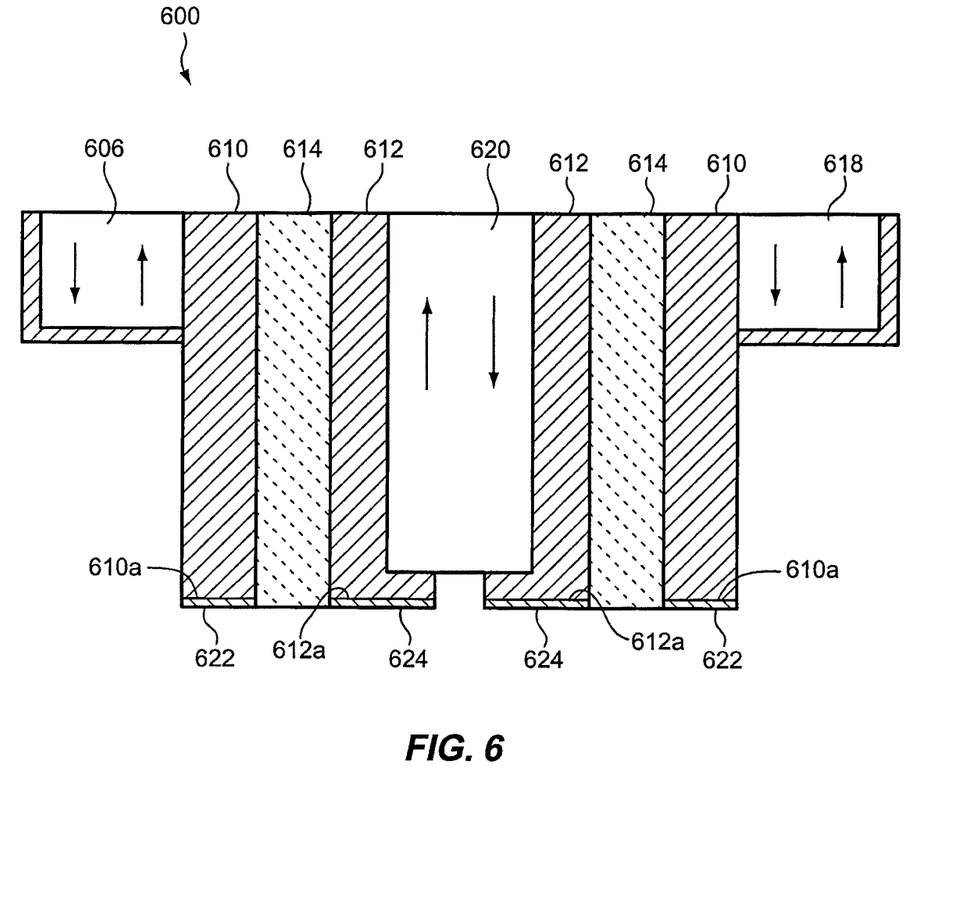
FIG. 6 is a schematic diagram of an applicator according to one embodiment of the invention in which the bottom surfaces of the microwave conducting elements are coated with electrically insulating but thermally conductive layers.

FIG. 6 schematically illustrates an applicator 600 according to another embodiment of the invention that includes two elongated microwave conducting elements 610 and 612, having generally tubular structures, that are coaxially positioned at a selected distance relative to one another. An electrically insulating element 614 separates the two conducting elements 610 and 612, and provides electrical insulation therebetween. The applicator 600 further includes chambers 606,

618, and 620 that allow bi-directional flow of a coolant fluid employed for cooling the electrodes 610 and 612, and consequently, corneal tissue treated with microwave radiation.

The conducting element 610 and 612 include bottom surfaces 610a and 612a, respectively, that are coated with layers 622 and 624, which are electrically insulating and thermally conductive. The coating layers 622 and 624 can be, for example, hard-coat anodized aluminum layers that electrically insulate the corneal tissue from the conducting elements 610 and 612 while allowing heat generated in the corneal tissue, e.g., in response to absorption of microwave energy applied by the applicator thereto, to be dissipated, e.g., by transfer to the coolant fluid flowing in the reservoirs 606, 618 and 620 via conducting elements 610 and 612. Each of the coating layers 622 and 624 can be deposited as a separate layer on the respective surface of the conducting elements on which it is disposed. Alternatively, each of the coating layers 622 and 624 can form a unitary structure with the surface on which it is disposed. For example, the conducting elements 610 and 612 can be formed of aluminum, and each of the coating layers 622 and 624 can be aluminum oxide layers formed, for example, by oxidizing a portion of each conducting element. Although a sharp boundary is depicted herein between each of the coating layers and the respective underlying surface of a corresponding microwave conducting element, in some embodiments, the elemental composition of the coating layer changes continuously across its boundary with the underlying surface of the conducting element from the composition in the bulk of the coating layer to that in the bulk of the conducting element on which the coating layer is disposed. In some embodiments, the coating layers 622 and 624 are plastic layers having a thickness in a range of about 0.001 inches to about 0.004 inches, and more preferably, in a range of about 0.001 inches to about 0.002 inches.

Figure 7:
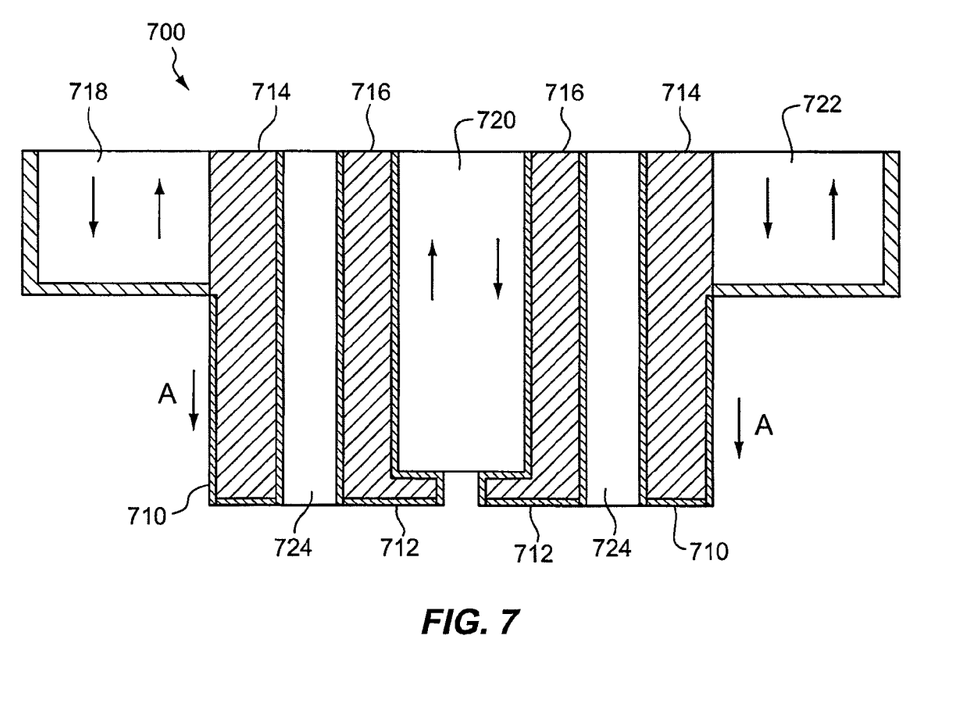
FIG. 7 is a schematic diagram of an applicator according to another embodiment of the invention in which the bottom surfaces of the microwave conducting elements, as well as at least a portion of a side surface of each conducting element, are coated with a thermally conductive and electrically insulating material.

FIG. 7 schematically depicts another embodiment of a microwave applicator 700 according to the teachings of the invention in which coating layers 710 and 712 not only cover bottom surfaces of microwave conducting elements 714 and 716, respectively, but they also extend along at least a portion of a tubular wall of each of these conductive elements. The coating layers 710 and 712 are preferably formed of an electrically insulating but thermally conductive material, e.g., hard-coat anodized aluminum. Such composition of the coating material allows the coating layers to insulate electrically corneal tissue from the conductive elements while facilitating transfer of heat from the corneal tissue to a coolant fluid circulating through chambers 718, 720, and 722. The device can be secured to the cornea via vacuum passage 724 and can include a contoured bottom to better conform to the corneal topography, if desired.

Although in many embodiments, the thermal conductivity of the coating layers 710 and 712 are substantially spatially uniform, in other embodiments, the coating layers exhibit a graded thermal conductivity. For example, the thermal conductivity of the coating layer 710 can increase in a direction A such that the portions of the coating layer that are closer to the corneal tissue have a higher thermal conductivity relative to those portions that are farther away. For example, when the coating layer is formed of alumina containing aluminum oxide particles in an aluminum matrix, the concentration of the aluminum oxide particles can vary in the coating, for example, it can be higher in portions closer to the applicator's distal end, so as to provide a desired gradation of thermal conductivity.

Figure 8:
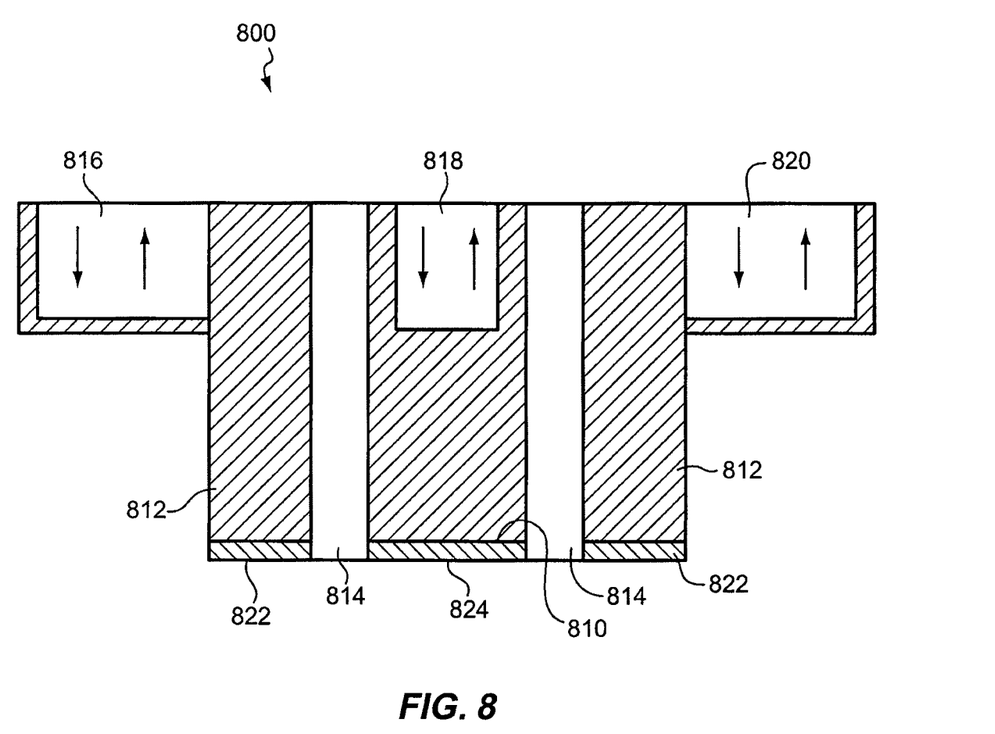
FIG. 8 is a schematic diagram of an applicator according to yet another embodiment of the invention in which the microwave conducting elements include a rod disposed within a conducting tube.

Referring to FIG. 8, another embodiment of an applicator 800 according to the teachings of the invention employs a microwave conducting rod 810, rather than a tube, as its inner microwave conducting element. The rod is disposed within an outer conducting tube 812 that forms the applicator's outer microwave conducting element. Similar to the previous embodiments, an electrical insulator 814 separates the outer conducting tube 812 from the inner conducting rod 810. Each of two chambers 816 and 820, thermally coupled to the outer conductive tube 812, allows bi-directional flow of a coolant fluid for extracting heat from the outer conducting tube 812. In addition, a chamber 818, which also allows a bi-directional flow of a coolant fluid, is thermally coupled to the inner rod for extracting heat therefrom.

The rod 810 can have a diameter in a range of about 2 mm to about 10 mm, and more preferably, in a range of about 6 mm to about 8 mm while the outer conducting tube 812 can have an inner diameter in a range of about 2.5 mm to about 12 mm, and an outer diameter in a range of about 3 mm to about 15 mm. In general, the rod's diameter is preferably selected to be larger than the pupil of the subject's eye. Further, the tubular insulating element 814 can have a thickness in a range of about 0.1 mm to about 2 mm, and more preferably in a range of about 0.5 mm to about 1 mm. This thickness defines the size of a gap between the rod 810 and the outer conducting tube 812.

A portion of one or both of the microwave conducting elements 810 and 812 can be coated with an electrically insulating material, which is preferably thermally conductive, to electrically insulate these elements from the corneal tissue upon positioning of the applicator on a subject's cornea. For example, in this exemplary embodiment, layers 822 and 824, formed of an electrically insulating and thermally conducting material, e.g., alumina, are disposed on bottom surfaces of the inner rod 810 and the outer tube 812, respectively, for providing electrical insulation.

Since certain changes may be made in the above methods and systems without departing from the scope hereof, it is intended that all matter contained in the above description or shown in the accompanying drawing be interpreted as illustrative and not in a limiting sense. It is also to be understood that the following claims are to cover generic and specific features described herein, and all statements of the scope of the invention which, as a matter of language, might be said to fall there between.

What is claimed is:

1. An applicator for providing eye therapy, comprising:
   a pair of electrical conducting elements electrically separated by a selected distance and extending from a proximal end to a distal end along an axis, the electrical conducting elements defining, at the distal end, a contact surface that is positionable at a cornea, at least one of the electrical conducting elements being divided into a plurality of discrete sections extending from the proximal end to the distal end; and
   a controller configured to selectively and separately actuate the discrete sections according to one or more variable characteristics to deliver energy to the cornea.

2. The applicator of claim 1, wherein the sections include longitudinally coextensive members separated from electrical contact with one another.

3. The applicator of claim 1, wherein at least one of the electrical conducting elements is divided in quartile sections of coaxial extension.

4. The applicator of claim 1, wherein the sections are separated by a dielectric material.

5. The applicator of claim 1, wherein the one or more variable characteristics includes at least one of intensity, duty cycle, waveform, frequency, and duration.

6. The applicator of claim 1, further comprising one or more sensors positioned to measure the one or more variable characteristics and providing feedback signals to the controller.

7. The applicator of claim 6, wherein the one or more variable characteristics including at least one of corneal elongation, corneal compression, corneal displacement, corneal velocity, corneal acceleration, local slope, local curvature, global slope, global curvature, corneal stress, and corneal pressure.

8. The applicator of claim 1, wherein at least two of the sections are actuated to have different levels of the one or more variable characteristics.

9. The applicator of claim 1, wherein the sections are actuated in unison.

10. The applicator of claim 1, further comprising a cooling system that cools the applicator.

11. The applicator of claim 1, further comprising a vacuum positioning system.

12. The applicator of claim 1, wherein the one or more characteristics provide modalities corresponding to a variety of diopter adjustments.

13. The applicator of claim 1, wherein the one or more characteristics provide treatment of astigmatism.

14. The applicator of claim 1, wherein the electrical conducting elements are concentric.

15. The applicator of claim 14, wherein at least one of the electrical conducting elements is a tube having, in a cross-section perpendicular to the axis, an annular shape.

16. The applicator of claim 1, wherein the sections are longitudinally coextensive, separated from electrical contact with one another, and have, in a cross-section perpendicular to the axis, a shape equal to a sector of an annulus.

17. The applicator of claim 16, wherein the sections are N in number, and the sector having a central angle of 180 degrees divided by N.

* * * * *